June 13, 1950 E. S. BOERNER Plant Pat. 949
ROSE PLANT
Filed April 22, 1949
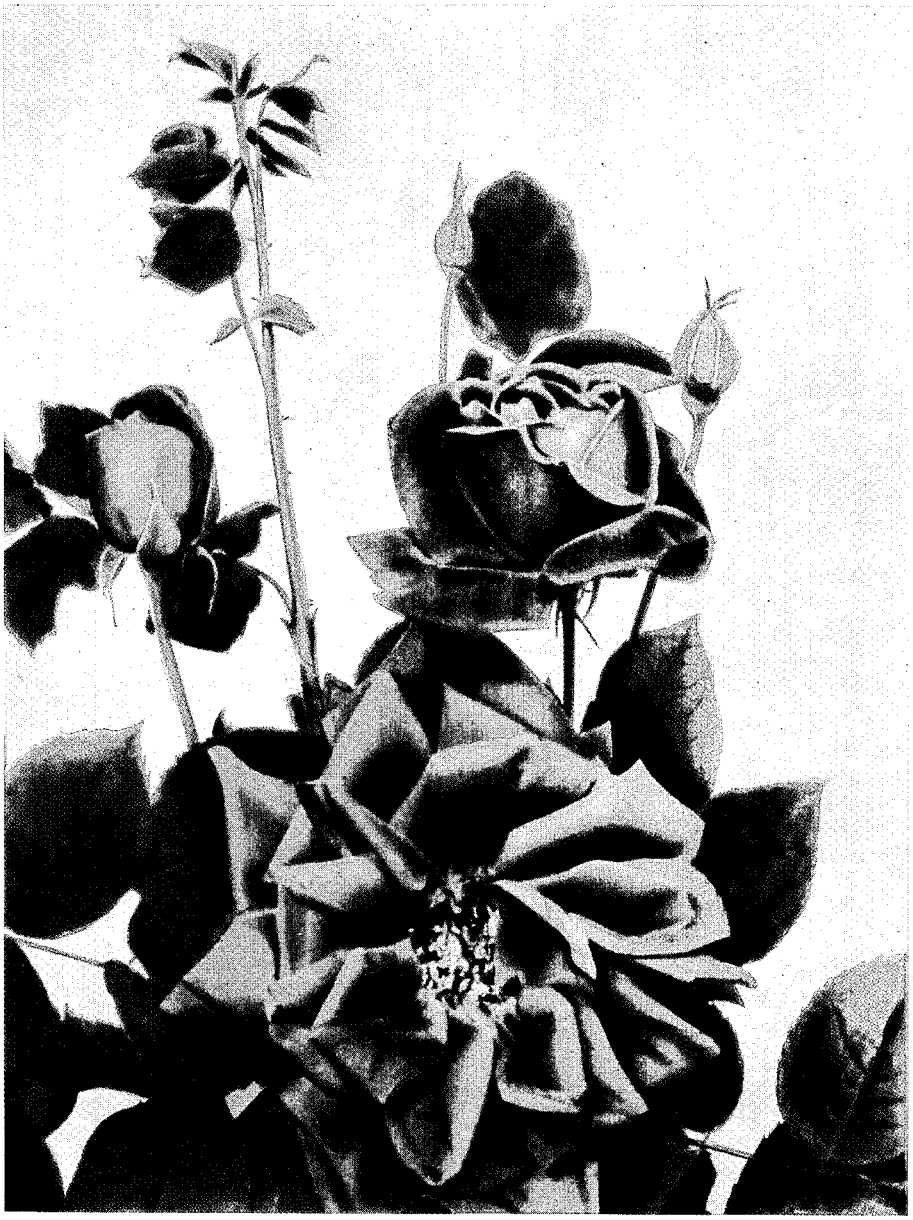
Inventor
E. S. Boerner
By Robb & Robb
Attorneys Patented June 13, 1950 Plant Pat. 949

UNITED STATES PATENT OFFICE

949

ROSE PLANT

Eugene S. Boerner, Newark, N. Y., assignor to Jackson & Perkins Company, Newark, N. Y., a corporation of New York Application April 22, 1949, Serial No. 88,920

1 Claim. (Cl. 47—61)

This invention relates to a new and distinct variety of rose plant, the object of said invention being to produce a new variety combining certain desirable characteristics of the parent varieties in an improved rose.

By crossing the varieties, "Crimson Glory" and "Ernie Pyle," I obtained a new flower color, a very dark rich red, notable for the dark, heavy velvety effect on the inside of the petals, and enhanced by the veining on the inside of the petals which seems to accent the velvety cast of the half-open flower. On the outside, the petals show a slightly contrasting red color combination and a stiff mid-rib.

Further distinctiveness is found in the Pomegranate Purple color of the filaments which is even deeper by several shades than the filaments of the pollen parent.

To these color distinctions may be added the very desirable characteristics of vigorous growth, extreme hardiness of the plant, and its freedom of bloom when planted outdoors.

Asexual reproduction of this new variety shows the foregoing characteristics come true to form and are established.

In the drawings are shown specimens of the blooms at different stages of development, from bud to fully opened flowers, with the dark velvety coloring as nearly as can be depicted.

The following is a detailed description of the new variety, color terminology being in accordance with Ridgway's Color Standards and Nomenclature:

Parentage: Seedling.

*Seed parent.*—"Crimson Glory" (Pl. Pat. No. 105).

*Pollen parent.*—"Ernie Pyle" (Pl. Pat. No. 673).

Classification: Botanic and commercial—hybrid tea.

Place where asexually reproduced: Newark, New York.

Method of reproduction: Budding.

*Flower*

(The following observations made in greenhouse at Newark, New York, in the morning in the month of December):

Blooming habit: Recurrent—continuous.

Bud:

*Size.*—Large.

*Form.*—Ovoid. Is not affected by wet or hot weather.

*Color.*—When sepals first divide—Oxblood Red, Plate 1. When petals begin to unfurl—Oxblood Red, Plate 1, overlaid with Pomegranate Purple, Plate 12. When half blown—inside of petals—Oxblood Red, Plate 1, overlaid with Pomegranate Purple, Plate 12; reverse of petals—Pomegranate Purple, Plate 12.

*Sepals.*—Serrated. Curl back when petals begin to unfurl. Color—inside—Kildare Green, Plate 31; outside—Light Bice Green, Plate 17.

*Calyx.*—Shape—pear. Size—small. Aspect—smooth. Odor when rubbed—none. Color—Oil Green, Plate 5.

*Peduncle.*—Length—long. Aspect—smooth. Color—Jade Brown, Plate 31. Strength—erect; heavy.

*Opening.*—Bud opens up well. Is not affected by adverse weather conditions.

Bloom:

*Size.*—Very large. Average size when fully expanded, 5½"-6".

*Borne.*—Singly.

*Stems.*—Long; strong.

*Form.*—When first open—high center. Permanence—all petals curl quill fashion when fully open.

*Petalage.*—Double (full but open center). Number of petals under normal conditions, 35.

*Color.* — Center of flower — Pomegranate Purple, Plate 12. Outer petals—Bordeaux, Plate 12, overlaid with Pomegranate Purple, Plate 12. Base of petals (aiglet)—Amber Yellow, Plate 16. Inside of petals—Pansy Purple, Plate 12, overcast with Pomegranate Purple, Plate 12, which gives a dark heavy velvety effect. This dark area shows a heavy veining. Reverse of petals—Pomegranate Purple, Plate 12, overcast with Spinel Red, Plate 26. General tonality from a distance—Pomegranate Purple, Plate 12.

*Discoloration.*—General tonality at end of first day—Pansy Purple, Plate 12, overcast with Pomegranate Purple, Plate 12. Second day—Pansy Purple, Plate 12, overcast with Pomegranate Purple, Plate 12. Third day—Pomegranate Purple, Plate 12.

Petals:

*Texture.*—Leathery with a prominent midrib on the outside of the petal and distinctive on the inside of the petal. Is not affected by wet or hot weather.

*Appearance.* — Inside — velvety; outside — Shiny.

*Form.*—Oval.

*Arrangement.*—Informal (with "rags" in center). Petaloids in center—few; large.

*Persistence.*—Drop off cleanly.

*Fragrance.*—Moderate. Nature—tea (average hybrid tea scent).

*Lasting quality.*—On the plant and as cut flower—long.

Genital organs:

*Stamens, anthers.*—Medium size; many. Color—Light Ochraceous Salmon, Plate 15. Arrangement—regular around styles.

*Stamens, filaments (threads).* — Long. Color—Pomegranate Purple, Plate 12.

*Pollen.*—Color—Pale Ochraceous Buff, Plate 15.

*Styles.*—Bunched, uneven length; medium length; thin.

*Stigmas.*—Color—Capucine Buff, Plate 3.

*Ovaries.*—All enclosed in calyx.

*Plant*

Form: Bush.

Growth: Vigorous; upright and branching.

Foliage 5–7 leaflets.

*Size.*—Large.

*Quantity.*—Abundant.

*Color.*—New foliage: upper side—Yellowish Citrine, Plate 16, lightly shaded with Oxblood Red, Plate 1; under side—Mignonette Green, Plate 31, overcast with Oxblood Red, Plate 1. Serrations—Oxblood Red, Plate 1. Old foliage: Upper side—Varley's Green, plate 18; under side—Cress Green, Plate 31.

*Shape.*—Oval pointed.

*Texture.* — Upper side — leathery; under side—Smooth. Ribs and veins—ordinary.

*Edge.*—Serrated (saw toothed).

*Serration.*—Single; small.

*Leaf stem.*—Color—Parrot Green, Plate 6. Under side—smooth.

*Stipules.*—Medium length; smooth.

*Disease resistance.*—Resistant.

Wood:

*New wood.*—Color—Yellowish Oil Green, Plate 5. Bark—smooth.

*Old wood.*—Color—Spinach Green, Plate 5. Bark—smooth.

Thorns:

*Thorns.*—Quantity on main stalks from base and on laterals from stalk—ordinary. Form — narrow base; medium length; hooked downward. Color when young—Deep Vinaceous, Plate 27. Position—irregular.

*Prickles and short needles.*—None.

I claim:

A new and distinct variety of rose plant characterized as to novelty by the color of its blooms, the veining of the petals on the inside and stiff mid-rib on the outside of the petals; its vigorous habit of growth, extreme hardiness and freedom of blooming when grown outdoors, substantially as shown and described.

EUGENE S. BOERNER.

No references cited.